(12) United States Patent
Ghoshal et al.

(10) Patent No.: US 7,238,791 B1
(45) Date of Patent: Jul. 3, 2007

(54) 6-MONOACETYLMORPHINE DERIVATIVES USEFUL IN IMMUNOASSAY

(75) Inventors: Mitali Ghoshal, Noblesville, IN (US); Gerald F. Sigler, Carmel, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/303,903

(22) Filed: Dec. 16, 2005

(51) Int. Cl.
*C07K 1/00* (2006.01)
(52) U.S. Cl. .................. 530/400; 530/402; 530/807
(58) Field of Classification Search ............ None
See application file for complete search history.

(56) References Cited

U.S. PATENT DOCUMENTS 5,843,900 A * 12/1998 Cheronis et al. ............ 514/15
6,262,265 B1    7/2001 Rouhani et al.

OTHER PUBLICATIONS

Hutchison, M. et al., "Diacetylmorphine degradation of 6-monoacetylmorphine and morphine in cell culture: implications for new in vitro studies," European Journal of Pharmacology 453 (2002) 27-32.
O'Neal, C. et al., "Simultaneous determination of Acetylcodeine, Monacetylmorphine and Other Opiates in Urine by GC-MS," Journal of Analytical Toxicology, vol. 21, Oct. 1997, 427-432.
Staub, C. et al., "Detection of Acetylcodeine in Urine as an Indicator of Illicit Heroin Use: Method Validation and Results of a Pilot Study," Clinical Chemistry 47:2 (2001) 301-307.

* cited by examiner

*Primary Examiner*—Cecilia J. Tsang
*Assistant Examiner*—Hemant Khanna

(57) ABSTRACT

Analogs of 6-monoacetyl morphine (6-MAM) are described. These include analogs derivatized at either the C-3 position, the C-6 position, or the nor position of the molecule. These analogs allow for elaboration with linkers terminated by a functional group such as an activated ester, the functional groups being useful for attaching the molecule to other entities such as proteins, polysaccharides, and reporter groups.

3 Claims, 8 Drawing Sheets

R = bovine serum albumin

6-MONOACETYLMORPHINE DERIVATIVES USEFUL IN IMMUNOASSAY

FIELD OF THE INVENTION

The present invention pertains to the field of drug monitoring, and in particular, to the field of detecting drugs of abuse in biological samples via immunoassay. More particularly, the present invention relates to chemical analogs of morphine useful in development of antibodies that recognize 6-monoacetyl morphine (6-MAM) and 6-monoacetyl codeine (6-MAC) and in production of conjugates useful in immunoassay methods for detection of 6-MAM and 6-MAC.

BACKGROUND OF THE INVENTION

Heroin (diacetylmorphine) is an opioid developed as an antitussive agent during the late nineteenth century. Heroin abuse soon became a problem and continues to be so now, more than a century later. Following ingestion, heroin is quickly metabolized to 6-monoacetyl morphine (6-MAM) and then to morphine, which in turn undergoes extensive metabolism.

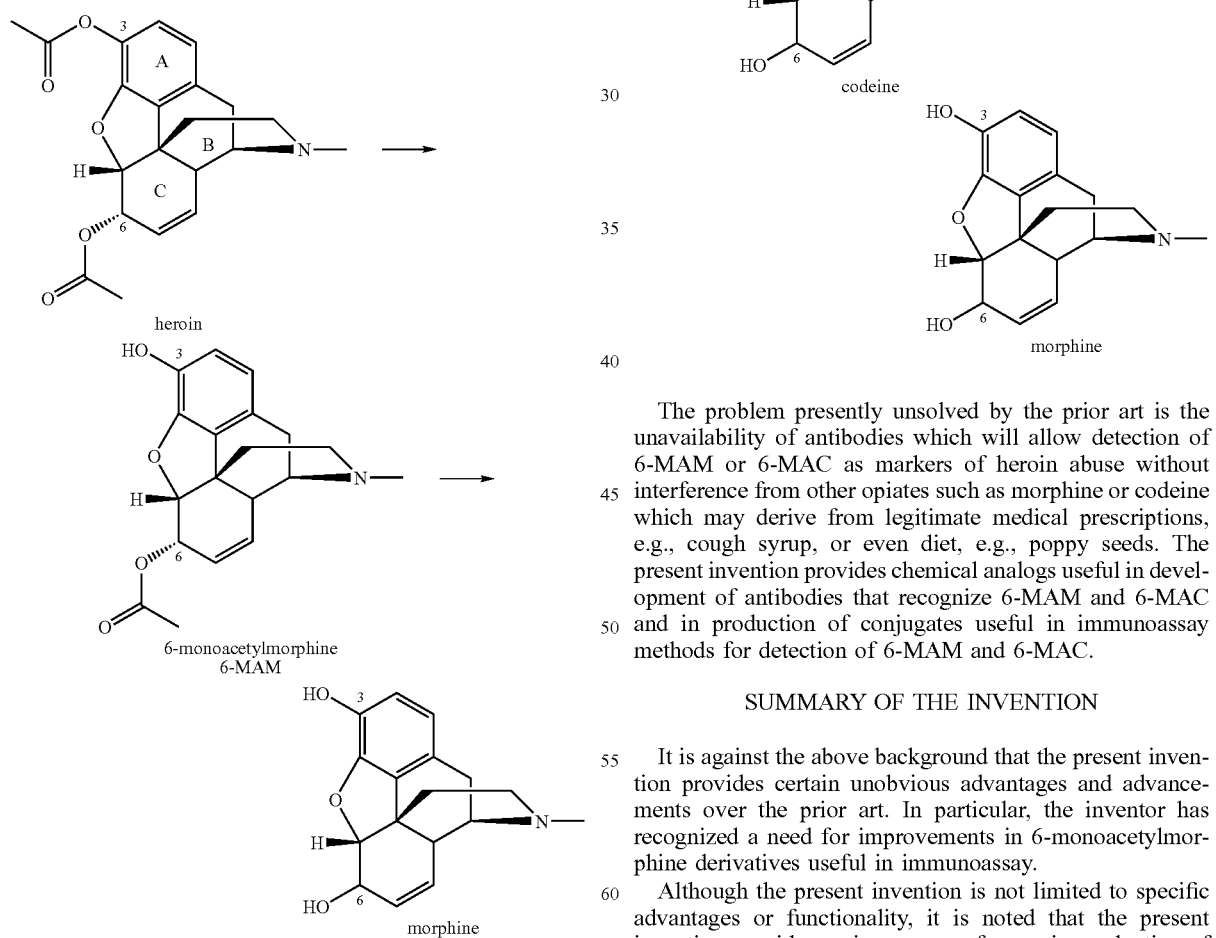

Acetylcodeine is a synthetic byproduct present in street heroin but not in pharmaceutical diacetylmorphine, which is used in heroin-assisted treatment for opiate dependent drug users. Acetylcodeine (AC) was investigated as a urinary biomarker for detection of illicit heroin use. Detection of acetylcodeine could play an important role in determining if addicts enrolled in heroin maintenance programs were supplementing their supervised diacetylmorphine doses with illicit heroin.

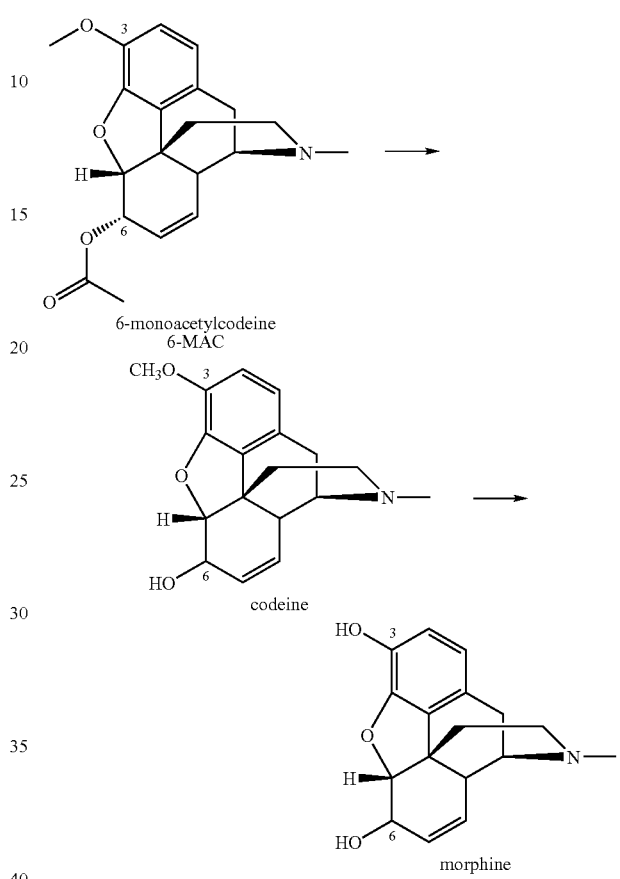

The problem presently unsolved by the prior art is the unavailability of antibodies which will allow detection of 6-MAM or 6-MAC as markers of heroin abuse without interference from other opiates such as morphine or codeine which may derive from legitimate medical prescriptions, e.g., cough syrup, or even diet, e.g., poppy seeds. The present invention provides chemical analogs useful in development of antibodies that recognize 6-MAM and 6-MAC and in production of conjugates useful in immunoassay methods for detection of 6-MAM and 6-MAC.

SUMMARY OF THE INVENTION

It is against the above background that the present invention provides certain unobvious advantages and advancements over the prior art. In particular, the inventor has recognized a need for improvements in 6-monoacetylmorphine derivatives useful in immunoassay.

Although the present invention is not limited to specific advantages or functionality, it is noted that the present invention provides an immunogen for use in production of an antibody that recognizes 6-monoacetylmorphine and 6-monoacetylcodeine. This immunogen is derived at the C-3 position of an analog of the 6-monoacetylmorphine molecule. An immunogen structure having a reduced double bond in the C-ring is also described.

In accordance with one embodiment of the present invention, a compound is provided having the structure:

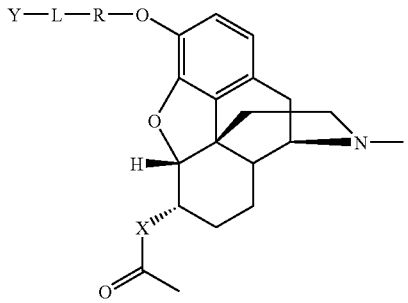

where R is a saturated or unsaturated, substituted or unsubstituted, straight or branched chain of 0-10 carbon or hetero atoms, L is a linker group consisting of 0-2 substituted or unsubstituted aromatic rings, and Y is an activated ester or NH—Z where Z is a carrier or label and X is NH or O.

In accordance with another embodiment of the present invention, a compound is provided having the structure:

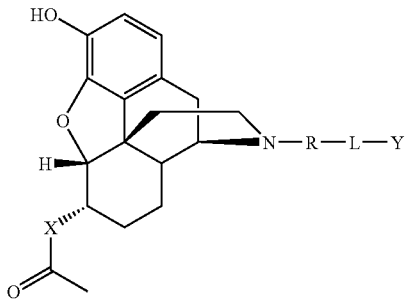

where R is $CH_2$ or C=O, L is a saturated or unsaturated, substituted or unsubstituted, straight or branched chain of 0-10 carbon or hetero atoms, and Y is an activated ester or NH—Z where Z is a carrier or label and X is NH or O.

In accordance with another embodiment of the present invention, a compound is provided having the structure:

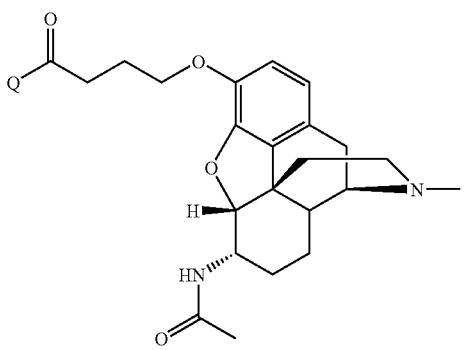

where Q is a carrier or label.

In accordance with another embodiment of the present invention, antibodies are provided which have specificity for 6-monoacetylmorphine and which are produced in response to a compound having the structure:

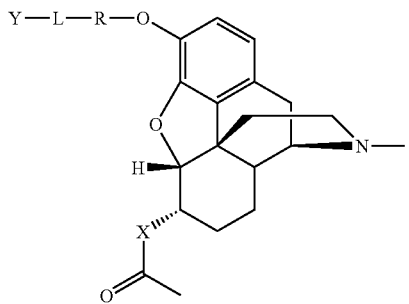

where R is a saturated or unsaturated, substituted or unsubstituted, straight or branched chain of 0-10 carbon or hetero atoms, L is a linker group consisting of 0-2 substituted or unsubstituted aromatic rings, X is NH or O, and Y is NH—Z where Z is a carrier.

In accordance with another embodiment of the present invention, antibodies are provided which have specificity for 6-monoacetylcodeine and which can be produced in response to a compound having the structure:

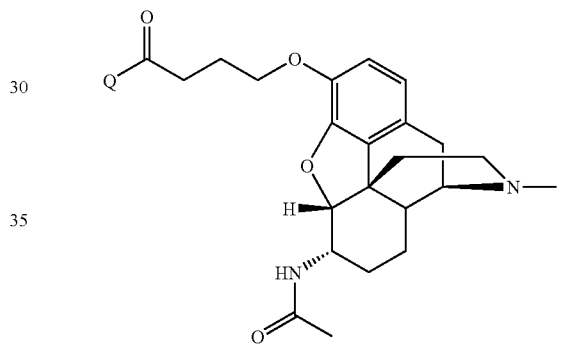

where Q is a carrier.

In accordance with another embodiment of the present invention, antibodies are provided which have specificity for 6-monoacetylmorphine and 6-monoacetylcodeine and which can be produced in response to a compound having the structure:

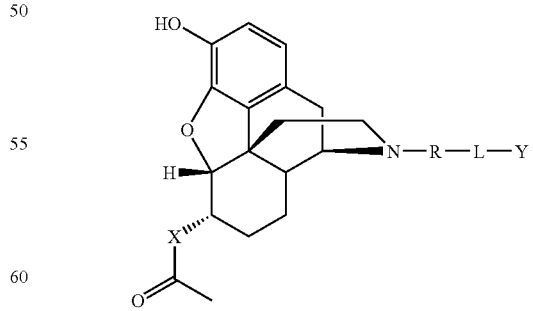

where R is $CH_2$ or C=O, L is a saturated or unsaturated, substituted or unsubstituted, straight or branched chain of 0-10 carbon or hetero atoms, X is NH or O, and Y is NH—Z where Z is a carrier.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings in which.

DETAILED DESCRIPTION OF THE INVENTION

Figure 1:
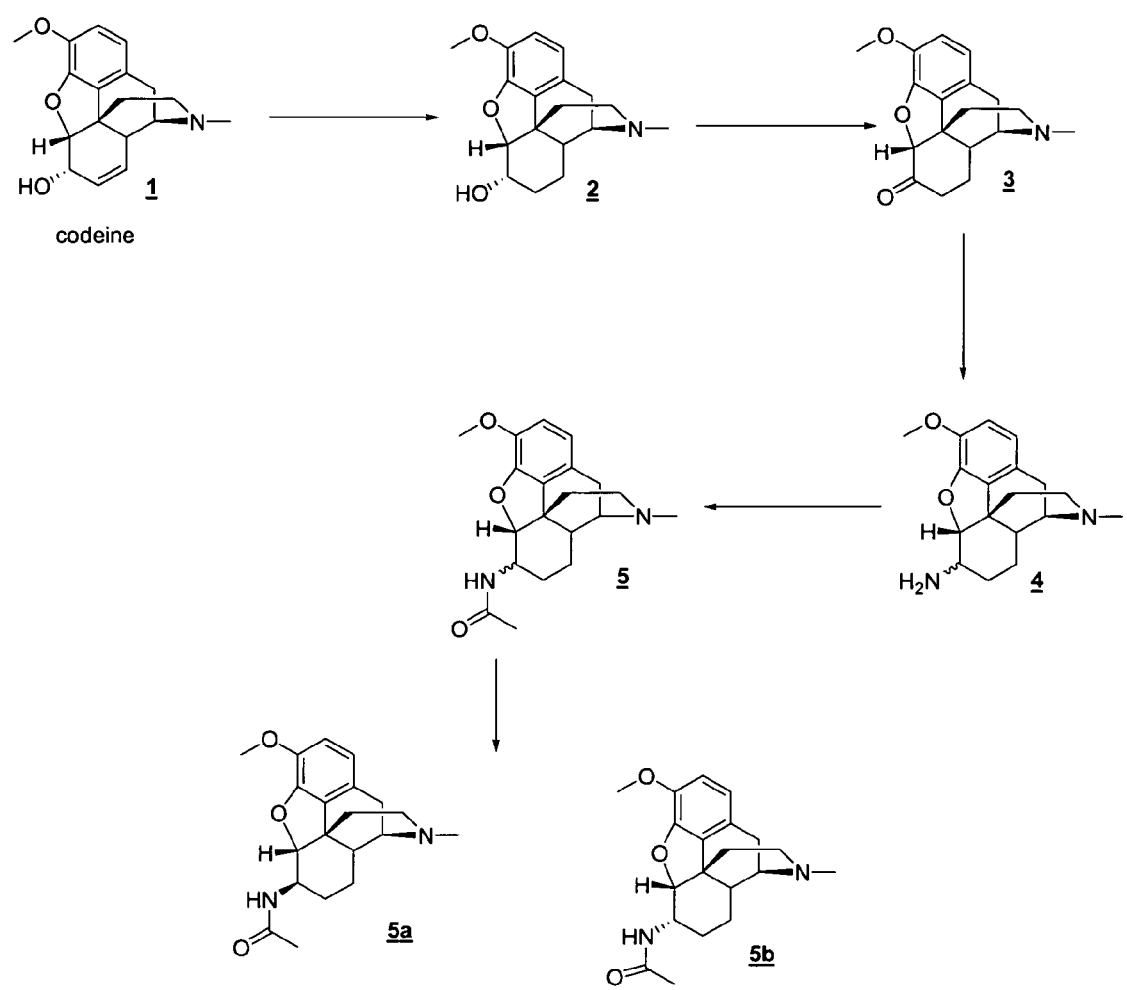
FIG. 1 is a schematic representation of the synthesis of 6-acetamido codeine intermediate.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

As used herein, the term "analyte" refers to a substance, or group of substances, whose presence or amount thereof is to be determined. As used herein, the term analyte subsumes the term "antigen", which refers to any compound that can bind to an antibody.

The term "antibody" means a specific binding partner of the analyte and is any substance, or group of substances, which has a specific binding affinity for the analyte to the essential exclusion of other unrelated substances. The term includes polyclonal antibodies, monoclonal antibodies, and antibody fragments.

The term "hapten" refers to a partial or incomplete antigen. Haptens are protein-free substances, mostly low molecular weight substances, which are not capable of stimulating antibody formation, but which do react with antibodies. The latter are formed by coupling a hapten to a high molecular weight carrier and injecting this coupled product into humans or animals. Examples of haptens include 6-monoacetylmorphine and 6-monoacetylcodeine.

The term "activated hapten" refers to a hapten that has been provided with an available reaction site, for example, by the attachment of a linking group carrying a reactive moiety, that can be used to connect the hapten to a carrier, immunogen, label, tracer, or other moiety.

The term "linker" refers to a chemical moiety that connects a hapten to a carrier, immunogen, label, tracer, or another linker. Linkers may be straight or branched, saturated or unsaturated carbon chains. They may also include one or more heteroatoms within the chain or at termini of the chains. By heteroatoms is meant atoms other than carbon which are chosen from the group consisting of oxygen, nitrogen, and sulfur. The use of a linker may or may not be advantageous or needed, depending on the specific hapten and carrier pairs.

A "carrier", as the term is used herein, is an immunogenic substance, commonly a protein, which can join with a hapten, thereby enabling the hapten to stimulate an immune response, or a substance that can form a conjugate useful in immunoassay, e.g., aminodextran and bovine serum albumin (BSA). Carrier substances include proteins, glycoproteins, complex polysaccharides, and nucleic acids that are recognized as foreign and thereby elicit an immunologic response from the host. Poly(amino acids) useful as carriers include keyhole limpet hemocyanin, bovine thyroglobulin, and bovine serum albumin.

The terms "immunogen" and "immunogenic" as used herein refer to substances capable of producing or generating an immune response in an organism.

The term "derivative" refers to a chemical compound or molecule made from a parent compound by one or more chemical reactions.

The term "conjugate" refers to any substance formed from the joining together of two parts. Representative conjugates in accordance with the present invention include those formed by the joining together of a small molecule and a large molecule, such as a protein. The term conjugate subsumes the term immunogen.

As used herein, a detector molecule, label, or tracer is an identifying tag which, when attached to a carrier substance or molecule, can be used to detect an analyte. A label may be attached to its carrier substance directly or indirectly by means of a linking or bridging moiety. Examples of labels include enzymes such as $\beta$-galactosidase and peroxidase, fluorescent compounds such as rhodamine and fluorescein isothiocyanate (FITC), luminescent compounds such as dioxetanes and luciferin, and radioactive isotopes such as $^{125}I$.

The term active ester within the sense of the present invention encompasses activated ester groups which can react with nucleophiles such as, but not limited to, free amino groups of peptides, polyaminoacids, polysaccharides, or labels under such conditions that no interfering side reactions with other reactive groups of the nucleophile-carrying substance can usefully occur.

An object of the present invention is to provide a compound having the structure:

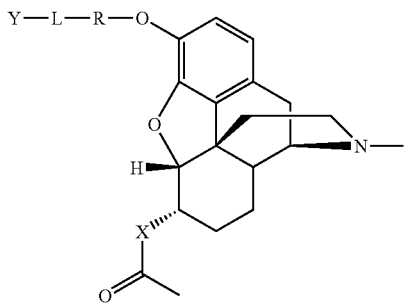

where R is a saturated or unsaturated, substituted or unsubstituted, straight or branched chain of 0-10 carbon or hetero atoms, L is a linker group consisting of 0-2 substituted or unsubstituted aromatic rings, and Y is an activated ester or NH—Z where Z is a carrier or label and X is NH or O.

Another object of the present invention is to provide a compound having the structure:

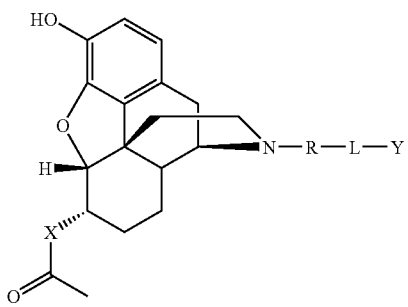

where R is CH$_2$ or C=O, L is a saturated or unsaturated, substituted or unsubstituted, straight or branched chain of 0-10 carbon or hetero atoms, and Y is an activated ester or NH—Z where Z is a carrier or label and X is NH or O.

Yet another object of the present invention is to provide a compound having the structure:

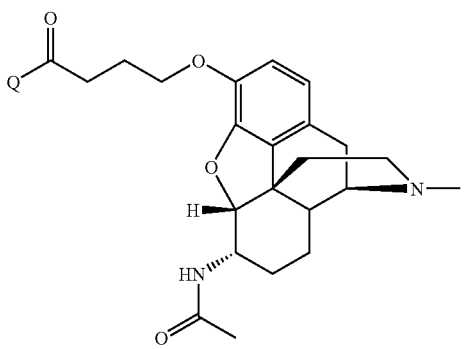

where Q is a carrier or label.

A further object of the present invention is to provide antibodies which have specificity for 6-monoacetylmorphine and which are produced in response to a compound having the structure:

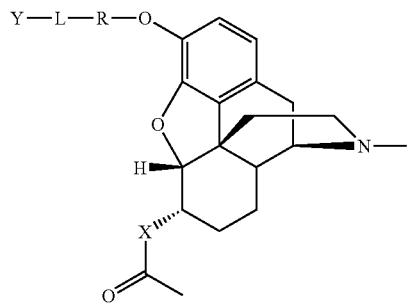

where R is a saturated or unsaturated, substituted or unsubstituted, straight or branched chain of 0-10 carbon or hetero atoms, L is a linker group consisting of 0-2 substituted or unsubstituted aromatic rings, X is NH or O, and Y is NH—Z where Z is a carrier.

A further object of the present invention is to provide antibodies which have specificity for 6-monoacetylcodeine and which can be produced in response to a compound having the structure:

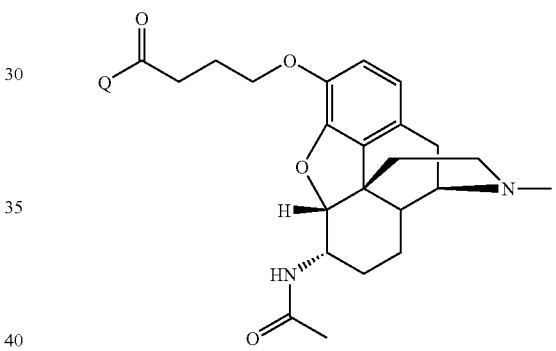

where Q is a carrier.

Yet a further object of the present invention is to provide antibodies which have specificity for 6-monoacetylmorphine and 6-monoacetylcodeine and which can be produced in response to a compound having the structure:

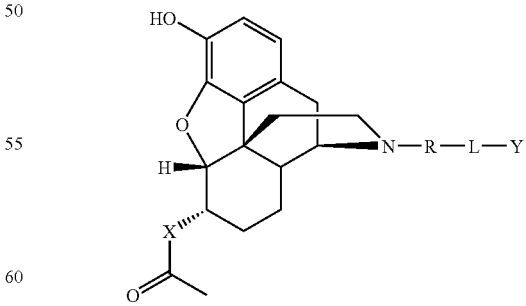

where R is CH$_2$ or C=O, L is a saturated or unsaturated, substituted or unsubstituted, straight or branched chain of 0-10 carbon or hetero atoms, X is NH or O, and Y is NH—Z where Z is a carrier.

The synthetic schemes for immunogens and screening conjugates of monoacetyl morphine and monoacetylcodeine are illustrated in FIG. 1 through FIG. 7.

Figure 2:
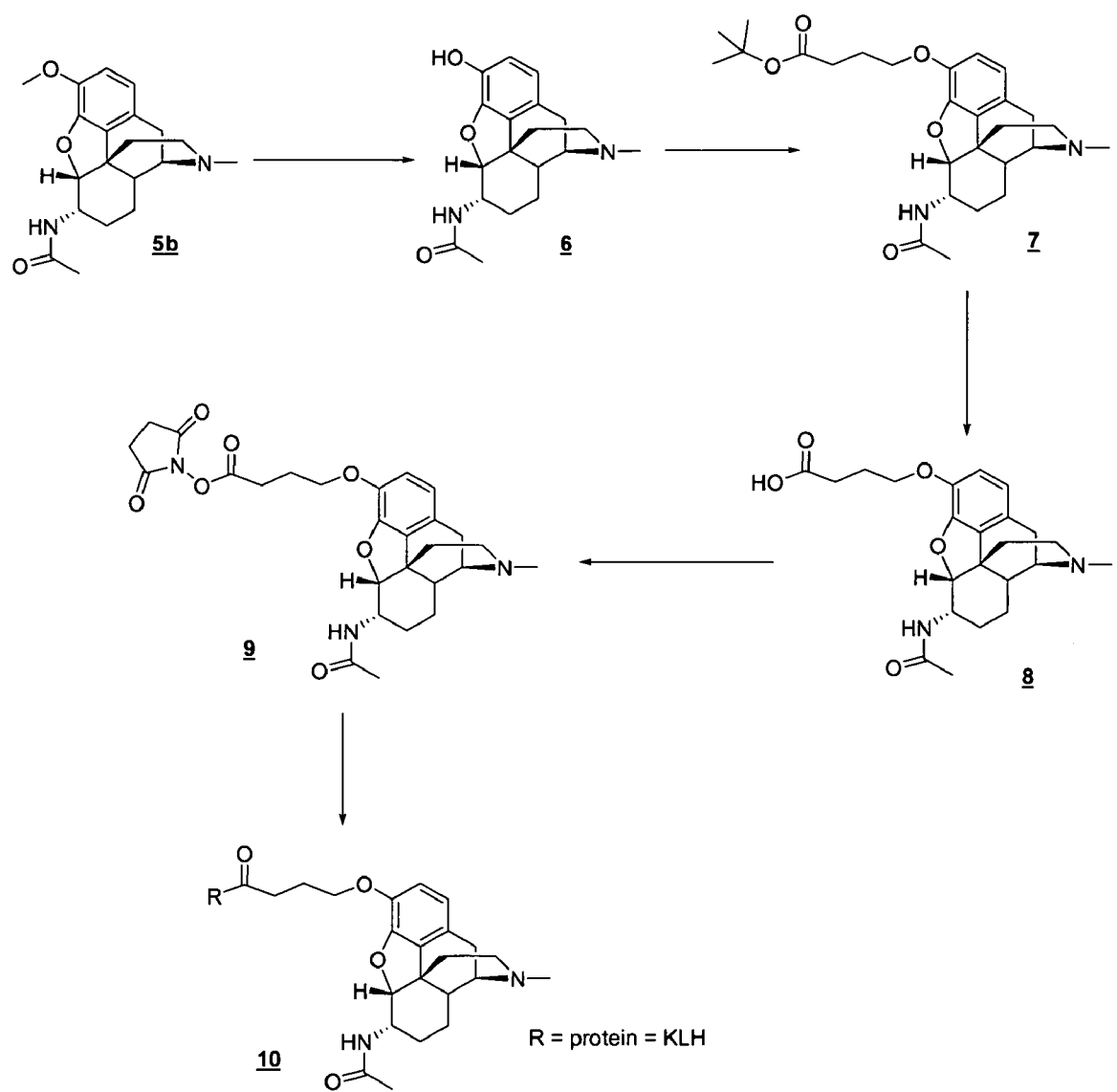
FIG. 2 is a schematic representation of the synthesis of 6-MAM analog immunogen out of 3-position.

Codeine is reduced to dihydrocodeine (see FIG. 1) using hydrogen gas, preferably palladium on charcoal as catalyst under pressure. Hydrogenation reactions are well known in the art and can be performed using many different catalysts such as Raney Ni, palladium hydroxide on charcoal, Adam's catalyst, etc in solvents such as methanol, ethanol, or ethyl acetate. The secondary hydroxyl group of dihydrocodeine is oxidized back to carbonyl group. Many literature references are known for conversion of a secondary hydroxyl group to carbonyl functionality, e.g., oxalyl chloride/DMSO, pyridinium chlorochromate and chromium oxide/pyridine, most preferably benzophenone and potassium t-butoxide under reflux conditions to give compound 3. The latter intermediate then undergoes reductive amination to give aminodihydrocodeine (4) in the presence of ammonium acetate and a reducing agent, sodium cyanoborohydride, preferably at a pH of 6 to 7, thus providing a mixture of two diastereomers (compound 4). Acetylation reaction of the amino group of compound 4 can be performed using acetic anhydride and pyridine at a temperature ranging from room temperature to reflux conditions. This reaction is performed using acetic anhydride as the acetylating agent and a base using triethylamine in the presence of 4-dimethylaminopyridine. The acetylated product is obtained as a mixture of diastereomers and can be separated by either column chromatography or preparative HPLC. Chromatographic techniques to separate diastereomers are well known in the art. The desired isomer (compound 5b) is demethylated to give the phenolic compound 6 (FIG. 2). A variety of demethylation reactions are known in the art, for example, trimethylsilyl iodide, sodium thioethoxide, potassium thiophenoxide, sodium cyanide in DMSO, aluminium tribromide in ethane thiol, aluminium chloride/dimethyl sulfide, and hydrobromic acid boron tribromide (Greene, T. and Wuts, P., "Protective groups in organic synthesis", $2^{nd}$ edition, Wiley Intersciences, 1991) at a temperature ranging from 0° to room temperature. Preferably the demethylation of the compound 5b is done in the presence of boron tribromide in dichloromethane at room temperature. The phenolic hydroxyl group of compound 5b is then extended with a protected carboxyl terminated linker through an ether linkage (FIG. 2). The phenolic hydroxyl group can also be converted to a carboxyl leashed linker by an ester or urethane linkage.

The t-butylester group of compound 7 is deprotected to a carboxylic acid functionality followed by conversion to an N-hydroxysuccinimide ester (compound 9). The activation of a carboxyl group can be accomplished by an activation step using a carbodiimide such as dicyclohexylcarbodiimide, 1-[3-(dimethylamino)propyl]-3-ethylcarbodiimide hydrochloride (EDC), or N,N,N',N'-O-succinimidyl-tetramethyluronium tetrafluoroborate. Conjugation to a protein provides an immunogen (compound 10) and screening conjugates.

Figure 3:
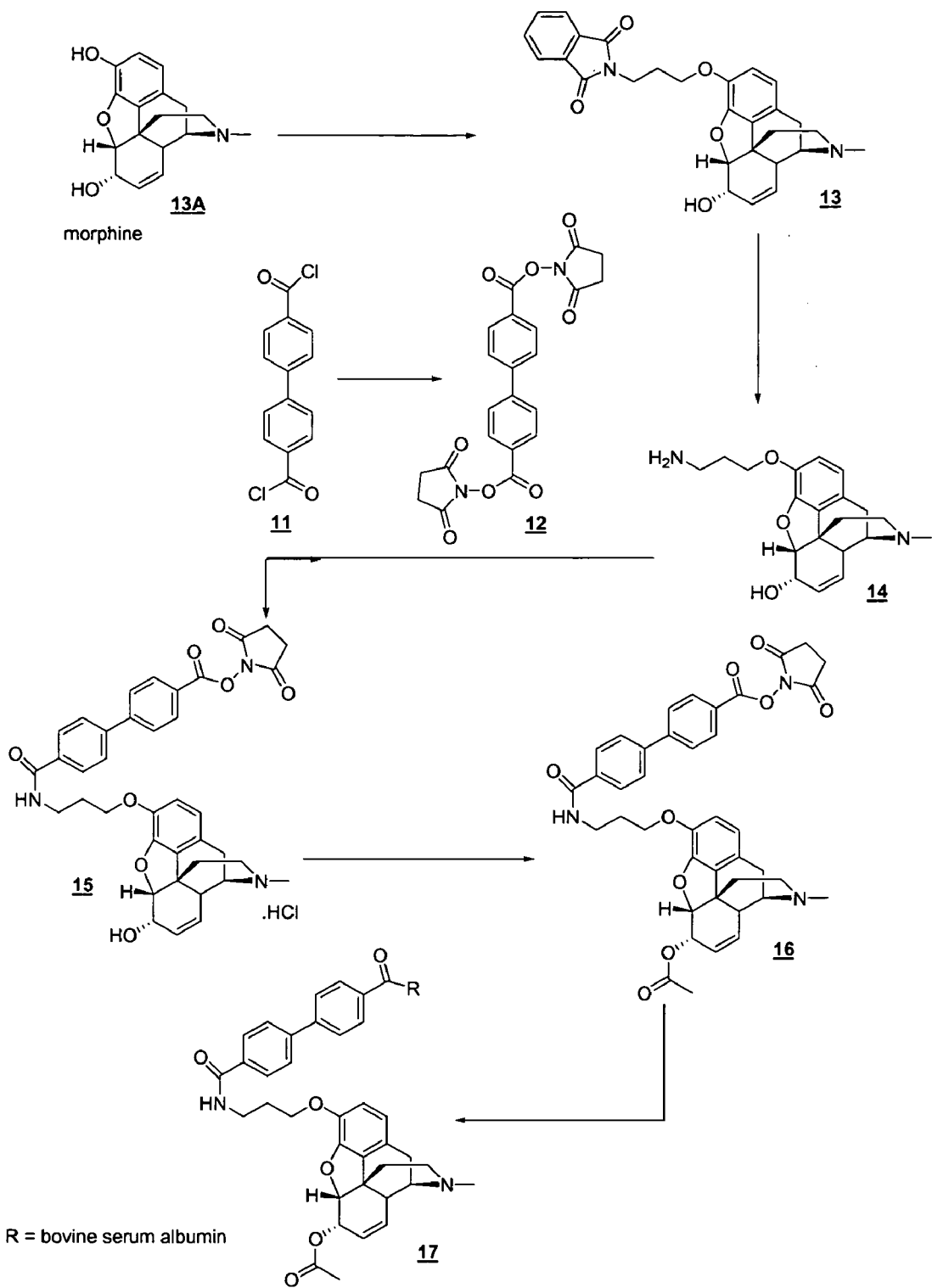
FIG. 3 is a schematic representation of the synthesis of 6-MAM screening conjugate out of 3-position.

The extension of the phenolic group can also be done using an alkylating reagent or acylating reagent with protected amino group (FIG. 3). An example of an amino protecting group is a phthalimido group, which can be cleaved under methyl amine or hydrazine. The amino group of the resultant amino leashed product is amenable to acylation reactions with a wide variety of carboxyl activated linker extensions or labels that are well known to those skilled in the art.

Linker extension is often performed to generate a terminal activating group. Linker extension using a homobifunctional linker such as N-hydroxysuccinimide ester of a biscarboxylic acid such as terephthalic acid or 4,4-bipenyl dicarboxylic acid (FIG. 3) can be used to generate an activated ester (compound 15) in a single step by reaction with the aforementioned amino group (compound 14). For a good treatise on the subject of linkers, the reader is referred to Hermanson, Greg T., "Bioconjugate Techniques", Academic Press Inc., 1996.

The 6-hydroxyl group of compound 15 is acetylated. Acetylation reaction can be done preferably using pyridine and acetic anhydride. The resulting active ester is conjugated to protein for use as a screening conjugate.

Figure 4:
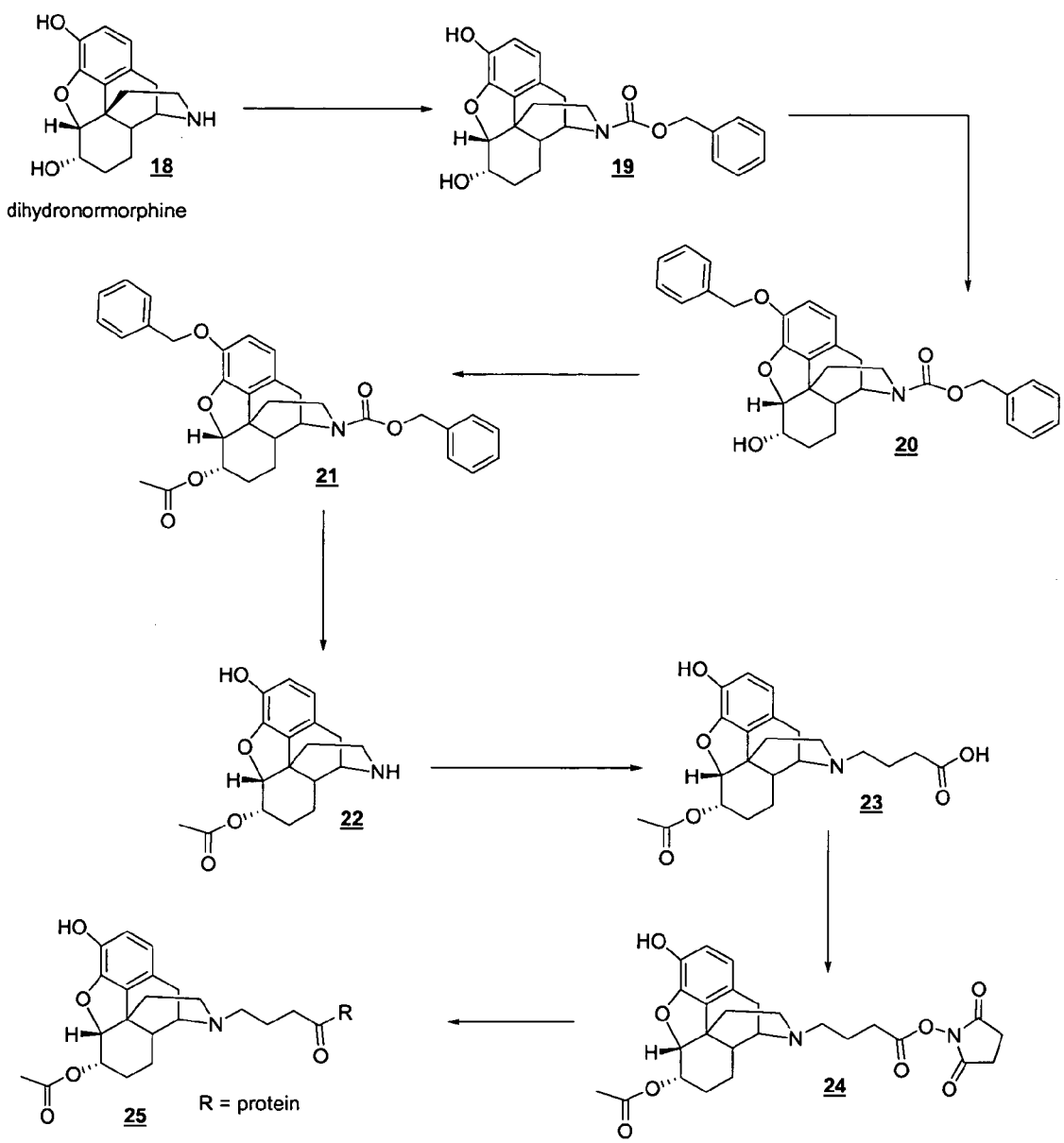
FIG. 4 is a schematic representation of the synthesis of 6-MAM 3-O-acetyl-N-position alkylated conjugate as an immunogen.

The immunogen leashed out of the nitrogen can use dihydronormorphine (compound 18) as a starting material. Protection of amino group in the presence of free phenolic hydroxyl group is known in the art. These reactions can be done by a proper choice of protecting group and reaction conditions. An example of an N-protecting group removed under mild basic conditions is fluoromethyloxycarbonyl (FMOC). An example of an N-protecting group easily removed with acid is t-butoxycarbonyl (BOC). An example of an N-protecting group removed under neutral hydrogenation conditions is a carbobenzyloxy group (CBz group). In this embodiment, the preferred protection of the cyclic secondary amine of dihydronormorphine is use of a carbobenzyloxy group in this sequence (FIG. 4). The phenolic group of CBz protected derivative (compound 19) can be protected as a benzyl group. The secondary hydroxyl group is then converted to an acetyl group (compound 21). One of the preferred acetylation reactions of the hydroxyl group is use of pyridine and acetic anhydride under reflux conditions. Deprotection of N-CBz and benzyl groups can be achieved in one step using hydrogen and palladium on a charcoal catalyst to give compound 22. The free secondary amine is extended to a carboxyl group though a succinylation reaction or a reductive amination reaction with succinic semialdehyde and sodium cyanoborohydride at a pH of 6-7. The compound 22 is then converted to an active ester (compound 23). The activation of a carboxyl group is accomplished by an activation step using a carbodiimide such as dicyclohexylcarbodiimide (DCC), EDC, or N,N,N',N'-O-succinimidyl-tetramethyluronium tetrafluoroborate. Conjugation to protein provides immunogen and screening conjugates.

Figure 5:
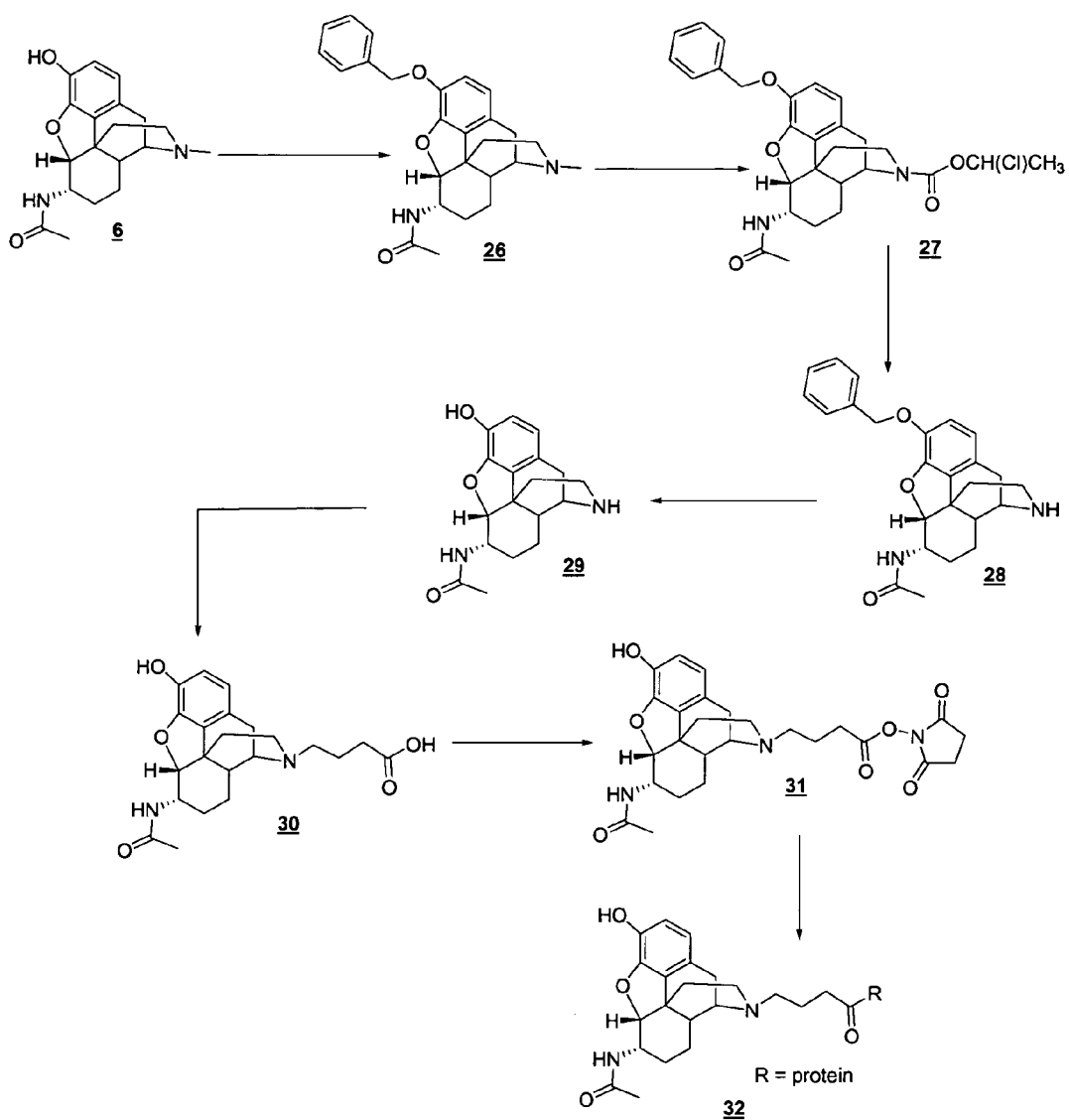
FIG. 5 is a schematic representation of the synthesis of 6-MAM-3-N-acetamido-N-position N-alkylated conjugate as an immunogen.

In a different embodiment, N-leashed 6-acetamido 6-MAM protein conjugate (FIG. 5 and FIG. 6) can also be made. The phenolic hydroxyl group of compound 6 can be protected as a benzyl group. N-demethylation of cyclic secondary amine is well known in the literature and can be achieved under various reaction conditions, such as 1-chloroethyl chloroformate followed by methanol, cyanogens bromide followed by Zn dust, or with vinyl chloroformate followed by treatment with hydrobromic acid. The preferred reaction used for N-demethylation of compound 26 is treatment of 1-chloroethyl chloroformate followed by methanol to give compound 28 (FIG. 5). Deprotection of the benzyl group is done under hydrogenation conditions using 10% palladium hydroxide on charcoal. Extension at the nitrogen position to a carboxyl terminal group by reductive amination (FIG. 5) followed by a carboxyl group activation procedure can be done as described earlier.

Figure 6:
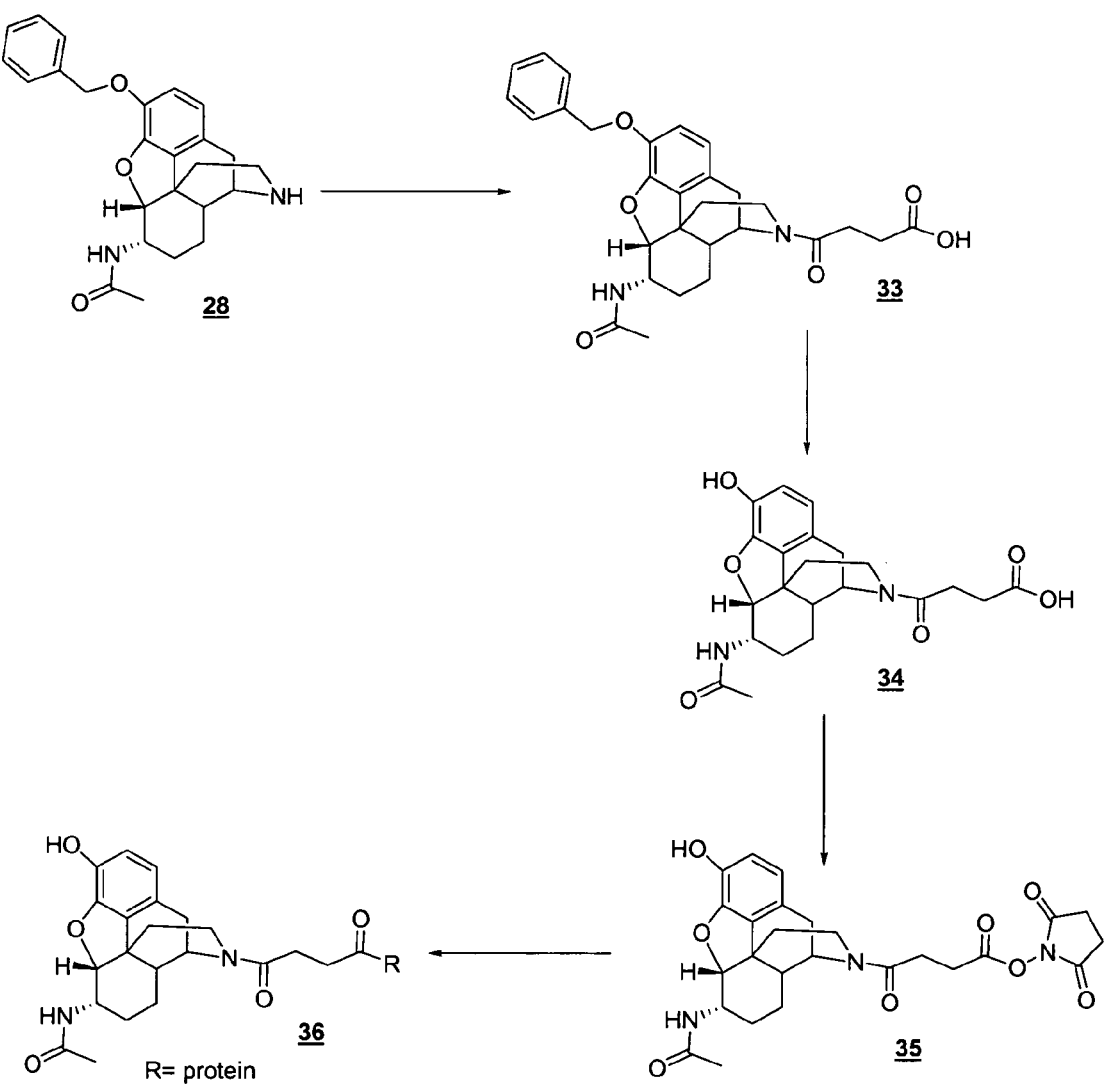
FIG. 6 is a schematic representation of the synthesis of 6-MAM analog-N-position N-acylated immunogen.

Extension at the nor position to a carboxy terminal group can also be achieved by succinylation of compound 28 to compound 33 (FIG. 6). Deprotection of the benzyl group followed by activation of the carboxylic group functionality can be achieved as described earlier.

Figure 7:
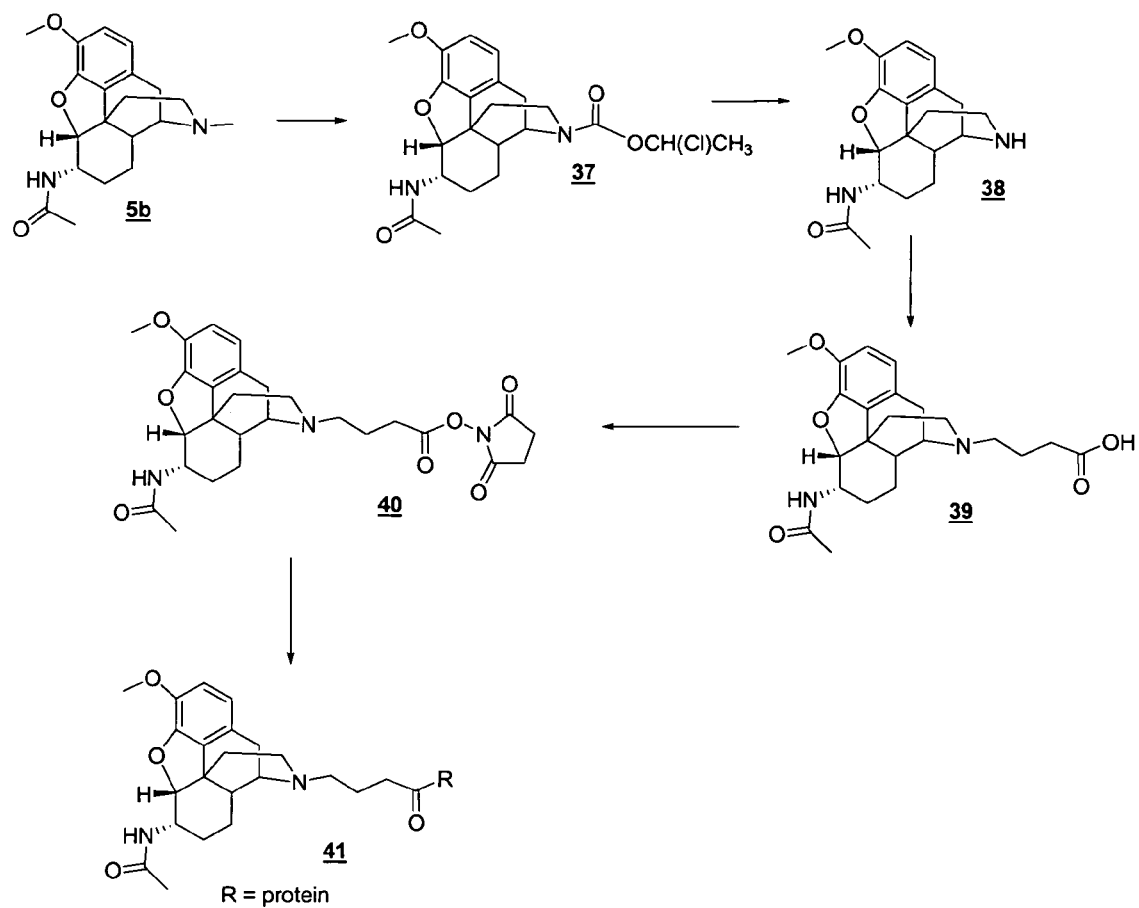
FIG. 7 is a schematic representation of the synthesis of 6-MAC-analog N-position immunogen.

FIG. 7 describes the preparation of a monoacetylcodeine immunogen. This can be used as a booster antibody for preparation of a 6-MAM antibody cross-reactive with 6-monoacetyl codeine. During the N-demethylation of compound 5b using 1-chloroethyl chloroformate in 1,2-dichloroethane, compound 38 was formed in one step. It was anticipated that the intermediate N-(1-chloroethoxy)carbonyl derivative (37) underwent hydrolysis under the reaction conditions to give compound 38.

Extension at the nor position to a carboxyl terminal functionality has been discussed earlier. Activation is followed by conjugation to a protein for preparation of the immunogen (compound 41).

In order that the invention may be more readily understood, reference is made to the following examples, which are intended to illustrate the invention but not limit the scope thereof.

Specific Embodiments

In the examples that follow, boldface numbers refer to the corresponding structure in the drawings.

EXAMPLE 1

Preparation of Dihydrocodeine (2)

To 1.2 g (4.0 mmol) of codeine in 40 mL of methanol was added 100 mg of 10% Pd—C. The resulting reaction mixture was hydrogenated under pressure of 50 psi. The solution was filtered through CELITE (Celite Corporation), and the filtrate was concentrated to give 1.12 g (3.7 mmol, 93%) of dihydrocodeinone as a white solid. ES (+) m/z 301.

EXAMPLE 2

Preparation of Dihydrocodeinone (3)

To a mixture of 1.25 g (11.1 mmol) of potassium-t-butoxide in 50 mL of benzene were added 6.78 g (37 mmol) of benzophenone and 1.12 g (3.7 mmol) of dihydrocodeine, which was allowed to reflux for 2 hours. The reaction mixture turned yellow. The reaction mixture was allowed to cool to room temperature, and 50 mL of 2N HCl was added. The resulting reaction mixture was allowed to stir for 10 minutes. The organic layer was separated and extracted with 3×40 mL of 2N HCl. The organic layer was discarded, and the aqueous layer was again extracted with 3×20 mL of dichloromethane. The aqueous layer was basified with aqueous potassium hydroxide solution to pH 12 and extracted with 5×60 mL of dichloromethane. The organic layers were combined and dried over $MgSO_4$ and filtered. The filtrate was concentrated to give 691 mg (2.3 mmol, 55%) of 3 as a yellow solid.

EXAMPLE 3

Preparation of Amino Dihydrocodeine (4)

To 3.46 g (11.5 mmol) of compound 3 in 70 ml of methanol was added 8.92 g (115 mmol) of ammonium acetate, which was and allowed to stir at room temperature for 15 minutes, at which time a clear solution was obtained. To the reaction mixture a solution of 727 mg (11.5 mmol) of sodium cyanoborohydride was added, and the pH of the reaction mixture was adjusted to pH 6-7 by addition of conc. HCl. The reaction mixture was allowed to stir at room temperature for 18 hours and concentrated under reduced pressure to give yellow oil. To this yellow oil 250 mL of water was added, and the pH was adjusted again to 1 with 6N HCl. The resulting aqueous reaction mixture was extracted with 2×250 mL of dichloromethane. The pH of the aqueous part was readjusted to 1 using 6N HCl and extracted with 3×250 mL of dichloromethane. The organic layers were combined, dried ($MgSO_4$), and concentrated to give 3.2 g (10.6 mmol, 92%) of 4 as a thick yellow oil. This product was used in the next step without purification.

HR-ES (+); calculated for $C_{18}H_{24}N_2O_2$, M+H 301.1911; observed 301.1913.

EXAMPLE 4

Preparation of Acetamido Dihydrocodeine Derivative (5B)

To 3.2 g (10.6 mmol) of amino dihydrocodeine 4 in 125 mL of dichloromethane were added 87 mg (0.71 mmol) of 4-dimethylaminopyridine and 9 mL of triethylamine. The reaction mixture was allowed to cool to 0° C., and 7.1 mL (74 mmol) of acetic anhydride was added. The reaction mixture was allowed to warm up to room temperature and allowed to stir for 18 h. The reaction mixture was concentrated under reduced pressure, and a yellow oil was obtained. To this yellow oil 125 mL of water was added, and the product was extracted with 4×150 mL of dichloromethane. The pH of the aqueous solution was adjusted to 10, and the solution was re-extracted with chloroform. All the organic layers were combined, dried ($MgSO_4$), and concentrated to give a colorless crude oil. LC-MS analysis indicated formation of two diastereomers. One half of the crude product was purified by RP-HPLC (C-18 column) using a gradient run with acetonitrile-water containing 0.1% trifluoroacetic acid. Fractions containing the desired isomer were combined and concentrated, followed by lyophilization to give 614 mg of product 5b as an off-white powder. HR-ES (+) calculated for $C_{20}H_{26}N_2O_3$, M+H 343.2016; observed 343.2022.

EXAMPLE 5

Preparation of Acetamido Dihydromorphine Derivative (6)

To 644 mg (1.8 mmol) of dihydrocodeine derivative (5b) was added 12 mL dichloromethane. This solution was added to a magnetically stirred solution of 11.3 mL (11.2 mmol) of 1M $BBr_3$ in 20 mL of dichloromethane at room temperature. The reaction mixture was allowed to stir at room temperature for 1 h and was poured into 60 mL of conc $NH_4OH$ solution and 30 g of ice. The reaction mixture was allowed to stir for 1 h and extracted with 5×100 mL of 80% ethanol in dichloromethane. The organic layers were combined, dried, and concentrated. The residue was purified by preparative RP-HPLC using a gradient run with acetonitrile-water containing 0.1% trifluoroacetic acid. Fractions containing the desired product were combined and concentrated followed by lyophilization to give 480 mg (78%, 1.46 mmol) of 6 as an off-white solid. LR-ES (+) M+H 329.

EXAMPLE 6

Preparation of Acetamido Dihydromorphine Butyric T-Butyl Ester Derivative (7)

To 50 mg (0.15 mmol) of acetamido dihydromorphine derivative (6) was added 6 mL of anhydrous acetone, 0.5 mL of anhydrous dimethylformamide, 150 mg (1.08 mmol) of potassium carbonate, and 140 µL (0.78 mmol) of t-butyl-bromobutyrate. The reaction mixture was allowed to reflux under argon atmosphere for 18 h, cooled to room temperature and filtered. The filtrate was concentrated under reduced pressure, redissolved in 60 mL of chloroform, and 25 mL of water was added. The organic part was separated, and the aqueous part was extracted with 3×50 mL of chloroform. All organic layers were combined, dried ($MgSO_4$), and concentrated. The residue was purified by silica gel flash column chromatography using 10% methanol in chloroform to give 35 mg (48%, 0.074 mmol) of 7 as a thick colorless oil. LR-MS-ES (+): M+H 471.

EXAMPLE 7

Preparation of Acetamido Dihydromorphine Butyric Acid Derivative (8)

To 35 mg (0.074 mmol) of acetamido dihydromorphine butyric acid derivative (7) was added 3 mL of dichloromethane and 1 mL of trifluoroacetic acid. The reaction mixture was allowed to stir at room temperature for 30 minutes and concentrated. To the residue 10 mL of dichloromethane was added and concentrated. The residue was purified by preparative RP-HPLC using a gradient run with acetonitrile-water containing 0.1% trifluoroacetic acid. Fractions containing the desired product were combined and concentrated followed by lyophilization to give 19 mg (0.045 mmol, 63%) of desired product 8 as white powder. HR-ES (+): Calculated for $C_{23}H_{30}N_2O_5$; M+H 415.2228; observed 415.2227.

EXAMPLE 8

Preparation of Acetamido Dihydromorphine Butyric Acid NHS Ester (9)

To 17 mg (0.041 mmol) of acetamido dihydromorphine butyric acid (8) was added 3 mL of freshly distilled THF and the mixture was cooled to 0° C. To the reaction mixture was added 21.4 µL (0.12 mmol) of N,N-diisopropylethylamine followed by 37 mg (0.12 mmol) of O—(N-Succinimidyl)-N,N,N',N'-tetramethyluronium tetrafluoroborate. The reaction mixture was allowed to warm up to room temperature and allowed to stir at room temperature 18 h. The reaction mixture was concentrated and the residue was purified by preparative RP-HPLC using a gradient run with acetonitrile-water containing 0.1% trifluoroacetic acid. Fractions containing the desired product were combined and concentrated followed by lyophilization to give 13 mg (0.02 mmol, 62%) of 9 as white solid. LR-MS-ES (+): M+H 512.

EXAMPLE 9

Preparation of 6-MAM KLH Conjugate (10)

A solution of 37 mg of keyhole limpet hemocyanin (KLH) in 1.2 ml of 50 mM potassium phosphate (pH 7.5) was cooled in an ice bath. To the reaction mixture 1.5 mL of DMSO was added dropwise, and the reaction temperature was maintained below room temperature. Then a solution of 8 mg (0.015 mmol) of 9 in 1 mL of DMF was added to the protein solution dropwise. The mixture was allowed to warm up to room temperature and was allowed to stir at room temperature 18 h. The resulting conjugate was placed in a dialysis tube (10,000 MW cut-off) and was dialyzed in 1 L of 70% DMSO in 50 mM potassium phosphate (pH 7.5, at least 3 hour), 1 L of 50% DMSO in 50 mM potassium phosphate (at least 3 hours), 1 L of 30% DMSO in 50 mM potassium phosphate (at least 3 h), 1 L of 10% DMSO in 50 mM potassium phosphate (at least 3 h) at room temperature followed by 50 mM potassium phosphate buffer (6 times, at least 6 h each at 4° C.). The protein concentration was determined to be 2.2 mg/mL using BioRad Coomassie blue protein assay (Bradford, M., Anal. Biochem. 72, 248, 1976). The extent of available lysine modification was determined to be 46% by the TNBS method (Habeeb AFSA, Anal. Biochem. 14, 328-34, 1988).

EXAMPLE 10

Preparation of 1,1'-biphenyl-4,4'-dicarbonyl Chloride (11)

A mixture of 10.0 g (0.041 mol) of 4,4'-biphenyldicarboxylic acid in 200 mL of anhydrous THF (distilled over Na and benzophenone) under argon was treated with 25.0 mL (0.286 mol) of oxalyl chloride followed by 0.1 mL of anhydrous DMF. The reaction was then concentrated at reduced pressure to a yellow oil. This was stripped down 5 times with anhydrous THF to drive off any residual oxalyl chloride to yield 11.5 g of the desired product 11 as a yellow solid. This was used in the next step without purification. MS: m/e 278 ($M^+$).

EXAMPLE 11

Preparation of 1,1'-biphenyl-4,4'-di-N-hydroxysuccinimide Ester (12)

A solution of 11.5 g (0.041 mol) of 11 in 500 mL of anhydrous dichloromethane under argon was treated with 25.0 g (0.217 mol) of N-hydroxysuccinimide followed by 25 mL of triethylamine and stirred at room temperature overnight. The resulting precipitate was collected by suction filtration and washed with dichloromethane to yield 10.7 g of product as a white solid. The filtrate was concentrated at reduced pressure, and the residue was triturated with dichloromethane to yield 3.84 g of a second crop as a white solid for a combined yield of 14.5 g (81%) of the desired product 12. MS m/e 437 (M+H).

EXAMPLE 12

Preparation of 3-O-Phthalimidopropyl Morphine (13)

1.5 g (37.5 mmol) of NaH (60% dispersion in mineral oil) was rinsed with 2×25 mL of hexanes to remove the oil. To the reaction mixture was added 140 mL of anhydrous DMF followed by 10.1 g (35 mmol) of morphine. This mixture was allowed to stir at room temperature for 30 minutes under nitrogen atmosphere, and 14.5 g (53 mmol) of N-(3-bromopropyl) phthalimide was added. The reaction mixture was allowed to stir 18 h at room temperature. The reaction was monitored by thin layer chromatography (silica, 7:2:1:1, MeOH:EtAc:NH4OH:$H_2O$, $I_2$ visualization), which showed that the reaction was incomplete. To the reaction mixture 0.15 g (3.75 mmol) of NaH (60% in oil) was added, and the mixture was allowed to stir for an additional 1.5 h. The mixture was poured into 350 mL of ice-water and extracted with 250 mL of ethyl acetate. The organic layer was separated, and the aqueous layer was extracted with 2×250 mL of ethyl acetate. The organic layers were combined and washed with 2×150 mL of water, 150 mL of 1N NaOH and 2×150 mL of water. The organic layer was dried (Na$_2$SO$_4$) and concentrated. The residue was crystallized with diethyl ether to give 12.9 g (27.3 mmol, 77%) of the desired product 13 as a white solid.

EXAMPLE 13

Preparation of 3-O-Aminopropylmorphine (14)

To 14 g (29.6 mmol) of 3-O-phthalimidopropyl morphine (13) was added 188 mL of 2M ethanolic methylamine, and the reaction mixture was allowed to stir for 3.5 h at room temperature under nitrogen. The reaction mixture was poured into 650 mL of chloroform and 425 mL of cold water. The organic layer was separated, and the aqueous layer was extracted with 3×90 mL of chloroform. The chloroform layers were combined and extracted with 2×140 mL of 1N HCl. The aqueous extract was basified with 140 mL of 2.5 N NaOH and extracted with 3×300 mL of chloroform. The organic layer was dried (Na$_2$SO$_4$) and concentrated. The residue was crystallized from diethyl ether to give 8.9 g (26 mmol, 88%) of 14 as a white solid.

EXAMPLE 14

Preparation of Morphine 3-O-Aminopropylbiphenyl N-Hydoxysuccinimide Ester Hydrochloride Salt (15)

To a mixture of 6.4 g (14.6 mmol) of biphenyl di-N-hydroxysuccinimide ester (12) in 400 mL of anhydrous THF was added a solution of 3.2 g (9.3 mmol) of 3-O-aminopropylmorphine (14) in 400 mL of anhydrous THF dropwise over a period of 30 minutes. The reaction mixture was allowed to stir at room temperature for 2 h and filtered. The filtrate was concentrated, and the residue was dissolved in 250 mL of dichloromethane. This was washed with 150 mL of saturated aqueous sodium bicarbonate solution, dried (Na$_2$SO$_4$), and concentrated. The residue was purified by silica gel column chromatography, first by eluting with ethyl acetate to remove the higher Rf impurities followed by eluting with anhydrous THF to give the desired product as a free base. All the fractions containing the desired product (Rf 0.13) were combined and treated with 12 mL of 1M HCl in ether. The solution was then concentrated at reduced pressure to give 3.2 g (49%, 4.5 mmol) of 15 as a white solid. MS: m/e 664 (M+H).

EXAMPLE 15

Preparation of 6-Monoacetylmorphine-3-O-Aminopropylbiphenyl N-Hydoxysuccinimide Ester (16)

To 50 mg (0.071 mmol) of morphine 3-O-aminopropylbiphenyl N-hydoxysuccinimide ester hydrochloride salt 15 was added 1 mL of anhydrous DMF, 7.1 μL of acetic anhydride, and 6.1 μL of anhydrous pyridine. The reaction mixture was allowed to stir 18 h. An analytical HPLC was run using RP-HPLC column (C-18) using acetonitrile and water containing 0.1% trifluoroacetic acid to monitor the progress of the reaction. The result indicated the presence of only starting material. To the reaction mixture 14 μL of acetic anhydride and 12 μL of pyridine were added. The mixture was allowed to stir for 6 h, and HPLC analysis indicated no reaction. To the reaction mixture 20 μL of acetic anhydride was added and allowed to stir 18 h. To the reaction mixture 0.5 mL of pyridine and 40 μL of acetic anhydride were added. The reaction mixture was allowed to stir at room temperature 18 h, and HPLC analysis indicated product formation. This was concentrated under reduced pressure to give a yellow oil and was purified by RP-HPLC (C-18 column) using a gradient run with acetonitrile-water containing 0.1% trifluoroacetic acid. Fractions containing the desired isomer were combined and concentrated followed by lyophilization to give 32 mg (64%, 0.04 mmol) of desired product 16 as white solid. HR-ES (+): calculated for C$_{40}$H$_{39}$N$_3$O$_9$, M+H 706.2759; observed 706.2758.

EXAMPLE 16

Preparation of 6-MAM BSA Conjugate (17)

To 500 mg of bovine serum albumin (BSA) was added 6 mL of 50 mM potassium phosphate, and the solution was allowed to cool to 0° C. To the reaction mixture 6 mL of DMSO were added dropwise for a period of 5 minutes. A solution of 13 mg (0.018 mmol) 6-MAM NHS ester derivative (16) in 1 mL of anhydrous DMF was added to the reaction mixture dropwise at 0° C. The mixture was allowed to warm up to room temperature and was allowed to stir at room temperature 18 h. The resulting conjugate was placed in a dialysis tube (10,000 MW cut-off) and was dialyzed in 1 L of 70% DMSO in 50 mM potassium phosphate (pH 7.5, 3 hours), 1 L of 50% DMSO in 50 mM potassium phosphate (at least 3 hours), 1 L of 30% DMSO in 50 mM potassium phosphate (at least 3 h), 1 L of 10% DMSO in 50 mM potassium phosphate (at least 3 h) at room temperature followed by 50 mM potassium phosphate buffer (6 times, at least 6 h each at 4° C.). The protein concentration was determined to be 15 mg/mL using BioRad Coomassie blue protein assay. The extent of available lysine modification was determined to be 46% by the TNBS method.

EXAMPLE 17

Preparation of N—CBz Nordihydromorphine (19)

To 200 mg (0.73 mmol) of dihydro normorphine (18) is added 12 mL of THF and 8 mL of water. To the reaction mixture 310 mg (2.92 mmol) of sodium carbonate is added followed by 0.12 mL (0.84 mmol) of benzylchloroformate. The mixture is allowed to stir at room temperature 18 h and concentrated under reduced pressure. To the residue 10 mL of water is added, and the pH is adjusted to 2 using 3N HCl. This is extracted with ethyl acetate, dried, and concentrated. The residue is purified by silica gel column chromatography to give 19.

EXAMPLE 18

Preparation of N—CBz-3-O-Benzyl-Nordihydromorphine (20)

To 100 mg (0.23 mmol) of compound 19 in 5 mL of anhydrous DMF is added 33 μl (0.27 mmol) of benzyl bromide, 55 mg (0.39 mmol) of potassium carbonate, and the reaction mixture is heated at 60° C. for 6 h, filtered, and the filtrate is concentrated. The residue is purified by silica gel column chromatography to give 20.

EXAMPLE 19

Preparation of 6-Acetyl
N—CBz-3-O-Benzyl-Nordihydromorphine (21)

To 100 mg (0.20 mmol) of 20 is added 1.5 mL of pyridine and 74 μL (0.78 mmol) of acetic anhydride. The reaction mixture is allowed to stir and is heated at 90° C. for 3 h. The resulting reaction mixture is allowed to cool to room temperature and concentrated. The residue is purified by silica gel column chromatography to give 21.

EXAMPLE 20

Preparation of 6-Acetyl-Nordihydromorphine (22)

To 100 mg (0.18 mmol) of compound 21 is added 30 ml of ethanol and 50 mg of 20% Pd(OH)$_2$/C. The reaction mixture is hydrogenated at 60 psi for 6 h. The reaction mixture is filtered through CELITE, and the filtrate is concentrated to give compound 22.

EXAMPLE 21

Preparation of 6-Acetyl Dihydronormorphine
N-Butyric Acid (23)

To 100 mg (0.31 mmol) of 6-acetyl dihydronormorphine (22) is added 25 mL of freshly distilled THF. The reaction mixture is allowed to stir at room temperature. 266 μl (0.38 mmol) of succinic semialdehyde (15 wt % solution in water) is added followed by 24 mg (0.38 mmol) of sodium cyanoborohydride. The pH of the reaction mixture is adjusted between 6-6.5, and the reaction mixture is allowed to stir at room temperature for 6 h. The reaction mixture is concentrated under reduced pressure, and 50 mL of dichloromethane is added followed by 25 mL of water. The organic layer is separated, and the aqueous layer is extracted with 2×50 mL of dichloromethane. The combined organic layers are dried and concentrated. The residue is purified by silica gel column chromatography to give 23.

EXAMPLE 22

Preparation of 6-Acetyl Dihydronormorphine
N-Butyric Acid N-Hydroxysuccinimide Ester (24)

To 100 mg (0.24 mmol) of 6-acetyl dihydronormorphine N-butyric acid (23) is added 30 mL of freshly distilled THF, and the mixture is cooled to 0° C. To the reaction mixture is added 0.10 ml (0.57 mmol) of N,N-diisopropylethylamine followed by 171 mg (0.57 mmol) of O-(N-succinimidyl)-N,N,N',N'-tetramethyluronium tetrafluoroborate. The reaction mixture is allowed to warm up to room temperature and is allowed to stir at room temperature 18 h. The reaction mixture is concentrated, and the residue is purified silica gel column chromatography to give 24.

EXAMPLE 23

Preparation of 6-Acetyl Dihydronormorphine
N-Butyric Acid KLH Conjugate (25)

This conjugate is prepared from compound 24 according to the procedure described for the conversion of compound 9 to compound 10.

EXAMPLE 24

Preparation of 6-Acetamido-3-O-Benzyl
Dihydromorphine (26)

To 500 mg (1.52 mmol) of 6 is added 12 mL of anhydrous DMF followed by 270 μL (2.26 mmol) of benzyl bromide and 734 mg (5.3 mmol) of anhydrous potassium carbonate. The reaction mixture is allowed to heat at 60° C. for 18 h, then is cooled to room temperature and filtered. The filtrate is concentrated and purified by preparative RP-HPLC using a gradient run with acetonitrile-water containing 0.1% trifluoroacetic acid. Fractions containing the desired product are combined and concentrated followed by lyophilization to give 26.

EXAMPLE 25

Preparation of 6-acetamido-3-O-Benzyl
N-[1-chloroethoxy carbonyl]Nordihydromorphine
(27)

To 250 mg (0.59 mmol) of 26 is added 5 mL of 1,2-dichloroethane. The resulting solution is allowed to stir, and 636 μL (5.8 mmol) of 1-chloroethyl chloroformate is added. The reaction mixture is heated under reflux conditions 18 h, and an additional 640 μL (5.9 mmol) of 1-chloroethyl chloroformate is added. The reaction is heated to reflux for 18 h and concentrated. The residue is used in the next step without purification.

EXAMPLE 26

Preparation of 6-Acetamido-3-O-Benzyl
Nordihydromorphine (28)

To all of the above [6-acetamido-3-O-benzyl N-[1-chloroethoxy carbonyl]nordihydromorphine (27)] is added 5 mL of methanol, and the mixture is allowed to heat to reflux for 6 h. The reaction mixture is concentrated, and the residue is purified by preparative RP-HPLC using a gradient run with acetonitrile-water containing 0.1% trifluoroacetic acid. Fractions containing the desired product are combined and concentrated followed by lyophilization to give 28.

EXAMPLE 27

Preparation of 6-Acetamido
3-OH-Nordihydromorphine (29)

To a solution of 100 mg (0.24 mmol) of 28 in ethanol is added 10% Pd-C, and the mixture is allowed to hydrogenate under 60 psi for 12 h. The reaction mixture is filtered, and the filtrate is concentrated to give 29.

EXAMPLE 28

Preparation of 6-Acetamido
3-OH-Nordihydromorphine N-Butyric Acid
Derivative (30)

Compound 30 is prepared from compound 29 following the procedure as described for the preparation of compound 23.

EXAMPLE 29

Preparation of 6-Acetamido 3-OH-Nordihydromorphine N-Butyric Acid NHS Ester Derivative (31)

This active ester is prepared from compound 30 according to the procedure used to convert the acid 23 to active ester 24.

EXAMPLE 30

Preparation of 6-Acetamido 3-OH-Nordihydromorphine N-Butyric Acid KLH Conjugate (32)

This conjugate is prepared according to the procedure described for conjugate 10.

EXAMPLE 31

Preparation of 6-Acetamido Nordihydrocodeine (38)

To 250 mg (0.73 mmol) of 5b was added 5 mL of 1,2-dichloroethane. The resulting solution was allowed to stir, and 636 µL (5.8 mmol) of 1-chloroethyl chloroformate was added. The reaction mixture was allowed to heat to reflux 18 h, and an additional 640 µL (5.9 mmol) of 1-chloroethyl chloroformate was added. The reaction mixture was heated under reflux conditions for an additional 18 h and concentrated. The residue was purified by preparative RP-HPLC using a gradient run with acetonitrile-water containing 0.1% trifluoroacetic acid. Fractions containing the desired product were combined and concentrated followed by lyophilization to give 75 mg (0.22 mmol, 31%) of 38 (M+H 329) as a white solid. [Note: The intermediate 6-acetamido-N-(1-chloroethoxy) nordihydrocodeine] derivative (37) was anticipated to be formed under reaction conditions and was hydrolyzed under reaction conditions].

EXAMPLE 32

Preparation of 6-Acetamido Nordihydrocodeine N-Butyric Acid (39)

This compound 39 is prepared from compound 38, following the procedure as described for the preparation of compound 23.

EXAMPLE 33

Preparation of 6-Acetamido Nordihydrocodeine N-Butyric Acid NHS Ester (40)

This active ester is prepared from compound 39 according to the procedure used to convert the acid 23 to active ester 24.

EXAMPLE 34

Preparation of 6-Acetamido-Nordihydrocodeine N-Butyric Acid KLH Conjugate (41)

This conjugate is prepared from 40 according to the procedure described for conjugate 10.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

EXAMPLE 35

Development of Monoclonal Antibodies to 6-Monoacetyl Morphine

Female Balb-c mice, at least 3 months of age, were used for immunizations. The immunogen contained 100 µg of the 6-MAM KLH immunogen from Example 9 per mouse emulsified in 50% isotonic saline and 50% Freund's Adjuvant. Complete Freund's Adjuvant was used for the initial intraperitoneal (ip) immunization, and Incomplete Freund's Adjuvant was used for the remaining immunizations. The mice were reimmunized 30, 84, and 114 days after the initial immunization. The mouse selected for the fusion was given a booster immunization identical to immunizations two through four 509 days after the first immunization. Four days later the immunized mouse was sacrificed, and its splenocytes were used in a cell fusion to produce monoclonal antibody secreting hybridomas.

The mouse selected for fusion was killed via exsanguinations and cervical dislocation, and the spleen was aseptically harvested and ground between two sterile glass slides to release the lymphocytes. The resulting lymphocyte suspension was fused with the P3X63Ag8.653 (ATCC cell line number CRL 1580) myeloma line.

Viable lymphocytes were counted, and 20% of that number of myeloma cells were added to the tube containing the mouse lymphocytes. The cells were washed in warm, serum-free Iscove's Modified Dulbecco's Media (IMDM) by centrifugation, resuspension, and re-centrifugation. The centrifuge tube containing the resulting pellet was gently tapped to loosen the pelleted cells. One ml of warmed PEG/DMSO solution (Sigma Chemicals) was then slowly added to the cells while gently mixing. The cells were incubated at 37° C. for 1.5 minutes after which pre-warmed serum-free IMDM was added at the following rates: 1 ml/min, 2 ml/min, 4 ml/min, and 8 ml/min. The tube was filled to 50 ml, capped, and incubated for 15 minutes at 37° C. The cell suspension was next centrifuged, the supernatant decanted, and the cells resuspended in HMT media. HMT media consists of Complete IMDM with Condimed (77.9% IMDM, 10% FCS, 10% Condimed H1, 1% L-glut, 1% L-glut-pen/strep, 50 uM 2-mercaptoethanol, 40 µM ethanolamine) with 50×HMT diluted to 1×). The cells were resuspended at a concentration of $2 \times 10^5$ lymphocytes/ml, and 200 µl were pipetted into each well of 30.5 sterile, covered 96-well microculture plates. The plates were incubated at 37° C. in 5% $CO_2$ tissue culture incubator for five days. On day six, 150 µl of supernatant was withdrawn from each well and was replaced with 150 µl of HT Rescue Media. HT Rescue Media consists of Complete IMDM with Condimed plus 50×HT supplement diluted to 1×. The plates were returned to the incubator and inspected daily for signs of growth. When cell colonies were sufficiently large, wells were screened for antibody production using an ELISA.

96-well microtiter plates were coated with 50 µl of the 6-MAM-BSA conjugate from Example 16 at 1 µg/ml in 0.1

M carbonate buffer, pH 9.5 for 1 hour at 37° C. (humidified). The plates were emptied, and 200 μl of post-coat solution consisting of pH 7.4 Tris buffer, 1% gelatin hydrolysate, 2% sucrose, and 0.18% TWEEN 20 were added. The plates were incubated 1 hour at 37° C. (humidified). After the plates were emptied, 200 μl of a 2% sucrose solution in 0.15M Tris, pH 7.4, was added. The plates were allowed to stand for approximately 5 minutes at room temperature and then were emptied and air dried overnight at room temperature. When dried, the plates were packed in zip-lock bags containing several desiccant pillows, sealed, and stored at 4° C. until use.

When clones were ready for testing, 20 μl of supernatant from each well showing cell growth was taken and transferred to 96-well flexible plates. PBST (phosphate buffered saline, pH 7.0, with 0.2% TWEEN 20) was added to each well to provide a 1:10 dilution of the supernatant sample. Two 6-MAM-BSA coated wells were used for each culture well tested. One well received 25 μl of PBST buffer, the other received 25 μl of PBST containing 6-MAM at a concentration of 800 ng/ml. Twenty-five microliters of the diluted sample were transferred to each pair of wells to assay supernatant antibody binding with and without free drug (6-MAM) present. The plates were incubated in a humid chamber for 1 hour at 37° C., after which they were washed with PBST. The wells were then filled with 50 μl of properly diluted goat anti-mouse IgG-HRP conjugate and again incubated for 1 hour. The plates were washed again, and 50 μl of K-Blue substrate was added. After a five minute incubation for color to develop, the reaction was stopped by the addition of 50 μl of 1 N HCl. Color was read via a microplate reader at 450 nm, and data was transferred to a computer for analysis. Supernatants that bound the 6-MAM-BSA conjugate (produced color in the wells) and showed significant inhibition of binding in the presence of free drug were considered positives, and the corresponding clones were subcloned. A total of 40 clones were selected for subcloning.

Subcloning was achieved by stringent cloning via limiting dilution. Briefly, cells from the original well were counted, and a dilution was made so that 120 cells were added to 40 mls of Complete IMDM with 10% Condimed.

These cells were then dispensed into 2 sterile 96-well plates, 200 μl per well. Wells containing colonies that appeared to have grown from single cells were screened on 6-MAM coated ELISA plates for binding in the absence of any free drugs and in the presence of morphine or codeine (each at 800 μg/ml). Clones from selected wells (positive for 6-MAM-BSA) were then expanded in culture and frozen to create a cell bank.

EXAMPLE 36

Use of 6-MAM 9.3 Monoclonal Antibody for Quantifying 6-MAM

Figure 8:
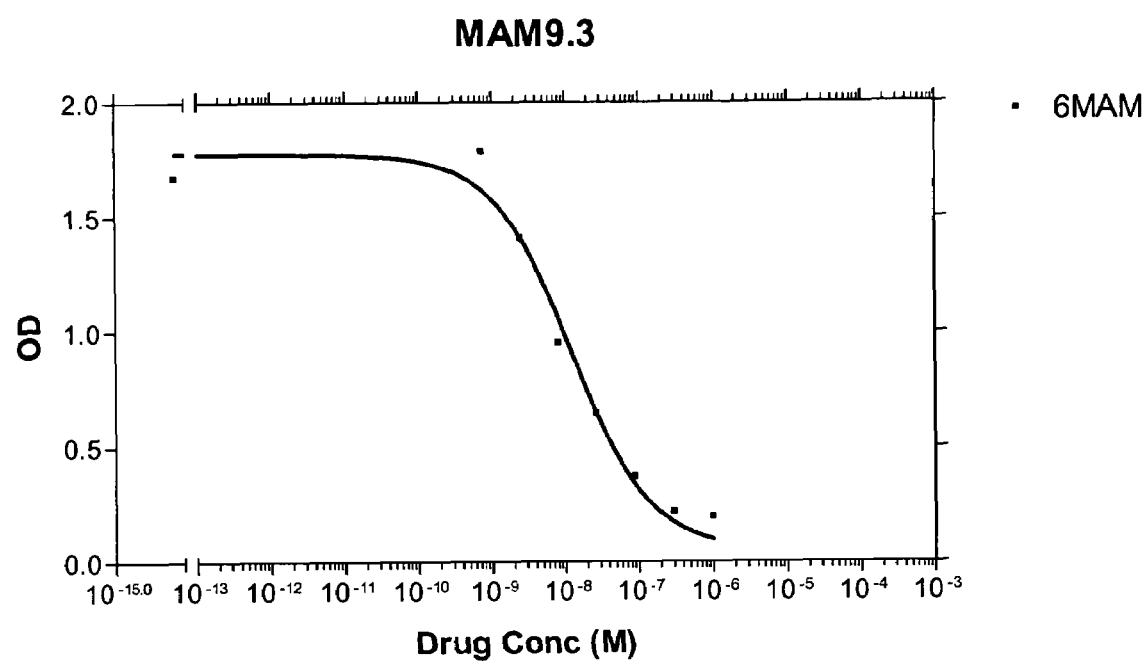
FIG. 8 is an inhibition curve generated using monoclonal antibody MAM 9.3 and varying concentrations of free 6-MAM.

6-MAM 9.3 was the third subclone selected from the 9$^{th}$ clone identified in the original fusion plates. Supernatant collected from 6-MAM 9.3 was titered on a 96-well plate coated with 6-MAM-BSA at 0.1 μg/ml. The dilution for the supernatant which provided for 90% of maximal OD was 1:270. 6-MAM 9.3 supernatant diluted 1:270 was then assayed on a 96-well plate coated with 0.1 μg/ml of 6-MAM-BSA with different concentrations of free 6-MAM added to the well to generate the inhibition curve shown in FIG. 8. The $ED_{50}$ was determined to be 1.22E-08. That parameter which describes the concentration of the free drug which corresponds to 50% of the binding in the absence of free drug is termed the $ED_{50}$ for that drug.

What is claimed is:

1. A compound having the structure:

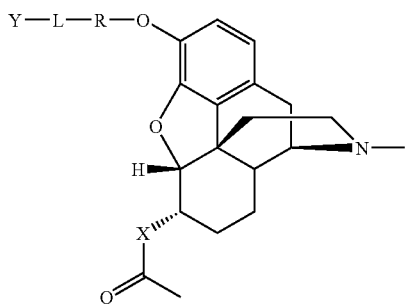

where R is a saturated or unsaturated, substituted or unsubstituted, straight or branched chain comprising 0-10 carbon or hetero atoms, L is a linker group comprising 0-2 substituted or unsubstituted aromatic rings, X is NH or O, and Y is an activated ester which can react with nucleophiles.

2. A compound having the structure:

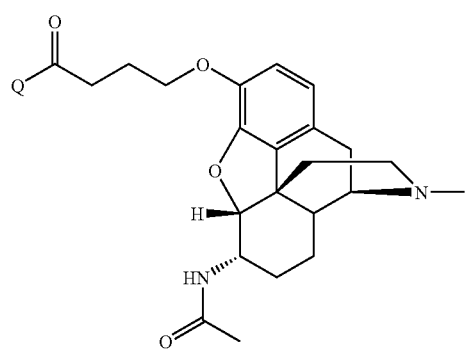

where Q is a carrier or label.

3. The compound of claim 2 wherein the carrier is selected from the group consisting of keyhole limpet hemocyanin, bovine thyroglobulin, bovine serum albumin, and aminodextran.

* * * * *